United States Patent [19]
Garber et al.

[11] Patent Number: 5,925,336
[45] Date of Patent: *Jul. 20, 1999

[54] AQUEOUS NAIL COATING COMPOSITION CONTAINING COPOLYMERIZED COLORANTS

[75] Inventors: Dennis Michael Garber, Jonesborough; James John Krutak, Sr., Kingsport, both of Tenn.

[73] Assignee: Eastman Chemical Company, Kingsport, Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/728,457

[22] Filed: Oct. 10, 1996

Related U.S. Application Data

[60] Provisional application No. 60/009,392, Dec. 29, 1995.

[51] Int. Cl.$^6$ .................................................. A61K 7/043
[52] U.S. Cl. ................................................................ 424/61
[58] Field of Search ...................................... 424/78.08, 61

[56] References Cited

U.S. PATENT DOCUMENTS

| | | | |
|---|---|---|---|
| 4,158,053 | 6/1979 | Greene et al. | 424/61 |
| 4,804,719 | 2/1989 | Weaver et al. | 525/420 |
| 5,240,780 | 8/1993 | Tiers et al. | 428/483 |
| 5,266,322 | 11/1993 | Myers et al. | 424/401 |
| 5,380,520 | 1/1995 | Dobbs et al. | 424/61 |

*Primary Examiner*—Peter F. Kulkosky
*Attorney, Agent, or Firm*—Jonathan D. Wood; Harry J. Gwinnell

[57] ABSTRACT

This invention relates to an aqueous nail coating composition and method for coloring nails comprising the use of a water-dispersible, colored sulfopolyester wherein the colorant moiety is incorporated into or onto a carbonyloxy and/or carbonylamide backbone of the sulfopolyester. The sulfopolyesters are uniquely designed to offer cosmetically desirable color coatings on nails.

39 Claims, No Drawings

AQUEOUS NAIL COATING COMPOSITION CONTAINING COPOLYMERIZED COLORANTS

CROSS REFERENCE TO RELATED APPLICATIONS

This application claims the benefit of provisional application Ser. No. 60\009,392, filed on Dec. 29, 1995.

FIELD OF THE INVENTION

This invention relates to an aqueous nail coating composition and method for coloring nails comprising the use of a water-dispersible, colored sulfopolyester wherein the colorant moiety is incorporated into or onto a carbonyloxy and/or carbonylamide backbone of the sulfopolyester.

BACKGROUND OF THE INVENTION

Many types of nail coating formulations are available. The majority of such nail coatings are lacquers which consist of a nitrocellulose, aryl sulfonamide formaldehyde resin, plasticizer and organic solvent mixture together with a small proportion of colorant and other ingredients. These nail lacquers have the disadvantages of poor moisture vapor transmission, discoloration of the nail, and require a long drying time. In addition, the nail lacquers contain volatile organic solvents which cause safety, toxicological and environmental concerns.

Film forming compositions have been disclosed in U.S. Pat. Nos. 4,939,233, 4,946,932 and 4,158,053. U.S. Pat. No. 4,939,233 discloses film forming compositions that contain a polyester having repeat units from at least one difunctional sulfomonomer containing at least one metal sulfonate group attached to an aromatic nucleus wherein the functional groups are carboxyl or hydroxyl, and an addition polymer having a majority of repeat units from vinyl acetate, wherein the later polymer is formed from monomers polymerized in an aqueous dispersion of said polyesters. The use of such compositions in nail polishes produce films which exhibit poor adhesion, poor durability and poor water resistance.

U.S. Pat. No. 4,946,932 discloses film forming compositions which contain an aqueous dispersion of a sulfonate group-containing polyester or polyesteramide and a polymer comprising repeat units from one or more $\alpha,\beta$-unsaturated monomers. The use of such compositions in nail polishes produces films which also exhibit poor adhesion, poor durability and poor water resistance.

U.S. Pat. No. 4,158,053 discloses aqueous nail coating formulations which are prepared by an aqueous emulsion polymerization of two or more monomers selected from alkyl acrylates, alkyl methacrylates and styrene compounds. The use of such formulations on nails produce slow drying films which exhibit poor adhesion and poor durability.

U. S. Pat. No. 5,266,322 discloses a nail coating composition prepared from an aqueous emulsion (A) which comprises a sulfopolyester and a copolymer of vinyl acetate and dialkyl maleate, and an aqueous emulsion (B) which comprises an aqueous emulsion of acetoacetoxyethyl methacrylate with a vinyl monomer. The nail coating composition has good adhesive properties and dries fast.

The coloring of nail polishes is discussed in Poucher's Perfumes, cosmetics, and Soaps, 9th ed., Chapman & Hall, N.Y. 1993, p. 252 which states that nail polishes are generally colored with insoluble pigments because water-soluble colorants are known to stain the skin. The difficulty with using insoluble pigments, however, is that the pigment must be exceedingly fine (<300 mesh) in order to remain in suspension during long storage periods. The required small particle size is attained by ball or roll milling which are energy-intensive, costly processes.

U.S. Pat. No. 4,804,719 discloses polymeric compositions which contain carbonyloxy and carbonylamide links, particularly polyesters and polyesteramides, having water solubilizing sulfonate groups and colorants copolymerized onto or into the polymer backbone. It is indicated that these polymers are useful in adhesives, coating materials, films and packaging materials. It is also stated that aqueous dispersions of these materials have utility as inks, paints and other industrial coatings, all of which are intended to be permanent in nature. No disclosure is made relating to the specific art of coloring nails, nonpermanently or otherwise.

Various examples of thermally stable industrial colorants useful for manufacturing colored polymers through incorporation into or onto the sulfopolyester polymer are described in U.S. Pat. Nos. 2,571,319; 3,104,233; 3,034, 920; 3,372,138; 3,417,048; 3,489,713; 3,278,486; 3,359, 230; 3,401,192; 3,417,048; 3,424,708; 4,049,376; 4,080, 355; 4,088,650; 4,116,923; 4,141,881; 4,202,814; 4,231, 918; 4,267,306; 4,279,802; 4,292,232; 4,344,767; 4,359, 570; 4,403,092; 4,477,635; 4,594,400; 4,617,373; 4,617, 374; 4,740,581; 4,745,173; 4,808,677; 4,892,922; 4,892, 923; 4,958,043; 4,999,418; 5,030,708; 5,032,670; 5,075, 491; 5,086,161; 5,102,980; 5,106,942; 5,151,516; 5,179, 207; 5,194,571; 5,274,072; 5,281,658, and 5,384,377. None of the above references suggest the application of such industrial colorants to human nails.

In summary, the water-dispersible colored sulfopolyesters used in this invention have chemical structures different from the colored polymers proposed as nail coatings in the prior art. The combination of water-solubilizing sulfonate groups, colored monomers, and the structure of the sulfopolyester backbone, which may include three to four additional monomers, is unique. Moreover, it is unexpected that such water-dispersible colored sulfopolyesters may be advantageously used for surface coloring of human nails. This result is unexpected due to the important differences in chemical composition and properties between the surface of human nails and the surfaces of cellulose based papers, containers and other man-made substrates onto which inks and paints are normally applied. Adequate wetting adhesion and film formation on the latter surfaces are no predictors of performance on the surface of human nails. In addition, other properties such as removal from the nail with soap and water, resistance to flaking and absence of skin staining could not have been expected from their industrial use as inks, paints or coatings, particularly since such applications are intended to be and are permanent.

SUMMARY OF THE INVENTION

Accordingly, it is an object of this invention to provide a composition and method for coloring nails using a colored sulfopolyester which forms a film wherein said film adheres to the surface of nails.

It is another object of this invention to provide a composition and method for coloring nails using a colored sulfopolyester which forms a film wherein said film remains flexible enough under different temperature and relative humidity conditions to withstand the bending of nails without fracturing and separating from the nail.

It is a further object of this invention to provide a composition and method for coloring nails using a colored sulfopolyester which forms a film wherein said film remains hard enough to prevent the transfer of color if the nail is rubbed against parts of the body, clothing, etc.

Another object of this invention to provide a composition and method for coloring nails using a colored sulfopolyester which forms a film wherein the film is relatively stable, nontoxic and does not irritate or stain the skin.

These and other objects of the invention are accomplished by a method of coloring nails comprising applying to the nail an effective amount of at least one water-dispersible sulfopolyester and a colorant reacted into or onto the sulfopolyester backbone. The sulfopolyester, containing substantially equimolar proportions of acid equivalents to hydroxy equivalents, comprises the reaction residues of the following reactants and their ester-forming derivatives:

(a) a dicarboxylic acid selected from the group consisting of aromatic dicarboxylic acids, saturated aliphatic dicarboxylic acids, cycloaliphatic dicarboxylic acids, and combinations thereof;

(b) a diol;

(c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino; and (d) from 1 to 40 mole %, based on a total of all acid and hydroxy equivalents being equal to about 200 mole %, of a colorant having the formula X—Col—X, wherein Col is the colorant residue, and X is a condensable carbonyloxy-reactive or carbonylamide-reactive substituent independently selected from the group consisting of hydroxy, carboxy, amino, alkylamino, an ester radical and an amido radical, wherein said radicals have the formula:

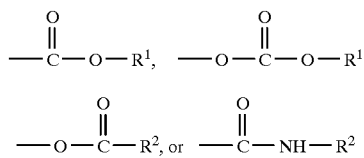

wherein $R^1$ is selected from the group consisting of $C_1$–$C_5$ alkyl, $C_3$–$C_8$ cycloalkyl and phenyl; and $R^2$ is hydrogen or $R^1$.

This invention is also directed to an aqueous nail coating composition comprising two aqueous emulsions. Aqueous Emulsion (A) contains the colored sulfopolyester and a copolymer containing vinyl acetate and a dialkyl maleate or fumarate, wherein the copolymer is polymerized in an aqueous dispersion of the colored sulfopolyester. Aqueous Emulsion (B) contains acetoacetoxyethyl alkylacrylate or a reaction product of acetoacetoxyethyl alkylacrylate with a vinylfunctional monomer.

DESCRIPTION OF THE INVENTION

The coloring of nails, preferably human finger and toe nails, is conveniently, quickly and safely provided by the method of the present invention, which comprises applying to the nail an effective amount of a water-dispersible colored sulfopolyester wherein the colorant is reacted into or onto the sulfopolyester backbone. As used herein, the term "effective amount" means an amount necessary for the naked eye to detect coloration.

The colored sulfopolyester of the present invention contains about 20 to about 100 mole % carbonyloxy linking groups in a linear molecular structure and 0 to about 80 mole % carbonylamide linking groups. The colored sulfopolyester has a number average molecular weight of from about 3,000 to about 15,000, more preferably from 4,000 to 10,000, and an inherent viscosity of from about 0.10 to about 0.50 measured in a 60/40 parts by weight solution of phenol/tetrachloroethane at 25° C. and at a concentration of 0.10 gram of polymer in 100 ml of the solvent. The colored sulfopolyester contains substantially equimolar proportions of acid equivalents (100 mole percent) to hydroxy and amino equivalents (100 mole percent), and comprises the reaction residues of a dicarboxylic acid, a diol, a difunctional sulfomonomer, and a colorant, and the ester-forming and esteramide-forming derivatives thereof.

The dicarboxylic acid component of the sulfopolyester is selected from aromatic dicarboxylic acids preferably having 8 to 14 carbon atoms, saturated aliphatic dicarboxylic acids preferably having 4 to 12 carbon atoms, and cycloaliphatic dicarboxylic acids preferably having 8 to 12 carbon atoms. Specific examples of dicarboxylic acids are: terephthalic acid, phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like. The sulfopolyester may be prepared from two or more of the above dicarboxylic acids.

It should be understood that use of the corresponding acid anhydrides, esters, and acid chlorides of these acids is included in the term "dicarboxylic acid".

The diol component of the sulfopolyester includes cycloaliphatic diols preferably having 6 to 20 carbon atoms or aliphatic diols preferably having 3 to 20 carbon atoms. Examples of such diols are: ethylene glycol, diethylene glycol, triethylene glycol, 1,4-cyclohexanedimethanol, propane-1,3-diol, butane-1,4-diol, pentane-1,5-diol, hexane-1,6-diol, 3-methylpentanediol-(2,4), 2-methylpentanediol-(1,4), 2,2,4-trimethylpentane-diol-(1,3), 2-ethylhexanediol-(1,3), 2,2-diethylpropane-diol-(1,3), hexanediol-(1,3), 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, and 2,2-bis-(4-hydroxypropoxyphenyl)-propane. The sulfopolyester may be prepared from two or more of the above diols.

The diol component of the sulfopolyester may also contain repeat units of poly(ethylene glycol) having the formula: $H(OCH_2CH_2)_nOH$ wherein n is an integer of from about 2 to about 500. Generally, the mole percent of the polyethylene glycol) added is inversely proportional to the quantity of n within said range.

The difunctional sulfomonomer component of the sulfopolyester may be a dicarboxylic acid or an ester thereof containing a sulfonate group (—$SO_3$—), a diol containing a sulfonate group, or a hydroxy acid containing a sulfonate group. The cation of the sulfonate salt may be Na+, Li+, K+, $NH_4$+, and substituted ammonium. The term "substituted ammonium" refers to ammonium substituted with an alkyl or hydroxy alkyl radical having 1 to 4 carbon atoms. The difunctional sulfomonomer contains at least one sulfonate group attached to an aromatic nucleus wherein the functional groups are hydroxy, carboxy or amino. Advantageous difunctional sulfomonomer components are those wherein the sulfonate salt group is attached to an aromatic acid nucleus such as benzene, naphthalene, diphenyl, oxydiphenyl, sulfonyldiphenyl or methylenediphenyl nucleus. Preferably the sulfomonomer is selected from sulfophthalic acid, sulfoterephthalic acid, sulfoisophthalic acid, 4-sulfonaphthalene-2,7-dicarboxylic acid, and their esters. The sulfomonomer is present in an amount from 4 to 25 mole percent based on 100 mole percent dicarboxylic acid and 100 mole percent diol.

Preferred results are achieved when the difunctional sulfomonomer component is 5-sodiosulfoisophthalic acid or its esters, and the diol is a mixture of ethylene glycol or 1,4-cyclohexanedimethanol with diethylene glycol.

The colorant component of the sulfopolyester contains one or more heat stable organic compounds initially having at least one condensable group. As used herein, the term "heat stable" means stable up to at least about 270° C. The colorant does not require milling and is insoluble in water after film formation. In addition, the colorant does not stain the skin. The colorant is present in an amount from about 1 to about 40 mole %, based on the total of all reactant hydroxy, carboxy and amino equivalents. These equivalents encompass the various condensable derivatives thereof including carbalkoxy, carbaryloxy, N-alkycarbamyloxy, acyloxy, chlorocarbonyl, carbamyloxy, N-(alkyl)$_2$carbamyloxy, alkylamino, N-phenylcarbamyloxy, cyclohexanoyloxy and carbocyclohexyloxy.

The colorant is represented by the formula:

X—Col—X wherein Col is the colorant residue having at least one functional group selected from hydroxy, carboxy and amino equivalents, and the condensable derivatives thereof, and X is a condensable carbonyloxy-reactive or carbonylamide-reactive substituent, i.e., a group reactive with at least one of the monomers from which the sulfopolyester is prepared. Examples of the reactive groups which X may represent include a hydroxy, carboxy, amino, alkylamino, an ester radical, an amido radical and the like. The ester radicals may be any radical having the formula:

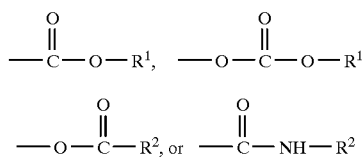

wherein $R^1$ is unsubstituted or substituted $C_1$–$C_5$ alkyl, $C_3$–$C_8$ cycloalkyl, phenyl or substituted phenyl. $R^1$ is preferably unsubstituted alkyl of up to about four carbon atoms, e.g. methyl and ethyl. $R^2$ is hydrogen or those groups listed for $R^1$. Typical substituents on the alkyl groups represented by $R^1$ and $R^2$ include hydroxy, $C_1$–$C_4$ alkoxy and halogen, phenyl, cyclohexyl, 2-furyl, cyano and halogen. Typical substituents on the phenyl groups represented by $R^1$ and $R^2$ include $C_1$–$C_4$ alkyl, $C_1$–$C_4$ alkoxy and halogen. Reactive group X preferably is hydroxy, carboxy, carbalkoxy or alkanoyloxy of up to about 4 carbon atoms, e.g. carbomethoxy or acetoxy. It is to be understood that X may represent two different reactive groups, e.g. one X group may represent hydroxy while the other X group may represent carboxy.

Suitable colorants are described in U.S. Pat. No. 4,804,719, the disclosure of which is incorporated herein by reference. The colorants may be made in a variety of colors, any of which may, in principle, be used either alone or in combination in preparing the nail coating compositions of this invention. The colorant is preferably selected from the classes of: methines; bis-methines; anthraquinones; 3H-dibenz[f,ij]isoquinoline-2,7-diones(anthrapyridones); triphenodioxazines; 5,12-dihydroquinoxalino[2,3-b] phenazines(fluorindines); phthaloylpyrrocolines; 2H-1-benzopyran-2-ones(coumarins); 3H-naphtho[2,1-b]pyran-2-ones(benzocoumarins); 4-amino-1,8 naphthalimides; thioxanthene-9-ones; 2,5(3)-arylaminoterephthalic acids (or esters); benzo[f]pyrido[1,2-a]indole-6,11-diones; quinophthalones; 7H-benz(de)anthracene-7-ones(benzanthrones); 7H-benzo[e]perimidin-7-ones (anthrapyrimidines); 6,15-dihydro-5,9,14,18-anthrazinetetrones (indanthrones); 7H-dibenz[f,ij]isoquinoline-7-ones (anthrapyridines); 6H,18H-pyrido[1,2-a:3,4-b']diindole-6,13-diones, diindolo [3,2,1-de:3',2',1'-ij][1,5]naphthpyridin-6,13-diones; naphtho [1',2',3':4,5]quino[2,1-b]quinazoline-5,10 diones; benzo[f] pyrido[1,2-a]indole-6,11-diones; 7H-benzimidazo[2,1-a] [de]isoquinolin-7-one; 5H-benzo[a]phenoxazine-5-ones; 5H-benzo[a]phenothiazine-5-ones; benzo[f]pyrido[1,2-a] indole-6,11-diones; 3,6-diaminopyromellitic acid diimides; naphthalene[1:4:5:8]tetra carboxylic bis imides; 3-aryl-2,5-dioxypyrrolines; perinones; perylenes; phthalocyanines; anthraisothiazoles; quinacridones; anthrapyrimidones; phthaloylacridones; phthaloylphenothiazines and phthaloylphenothiazine-S,S-dioxides.

Particularly preferred classes of colorants are the methines, bis-methines, anthrapyridones, anthraquinones and phthalocyanines. More than one colorant may be incorporated into the colored sulfopolyester.

The colored sulfopolyester is prepared according to the technology for preparing sulfo-containing polymers as described in U.S. Pat. Nos. 3,546,008; 3,734,874; 3,779,993; 4,233,196; 4,335,220; and, in particular, U.S. Pat. No. 4,804,719, the disclosures of which are incorporated herein by reference.

The concentration of the colorant in the final nail coating composition will vary, depending upon both the concentration of the dye moiety in the polymeric colorant and the inherent intensity of the color of the dye moiety. In general, the dye moiety may constitute between 1% and 40% by weight of the final polymeric colorant. Preferably it will be between 10% and 30%.

The colored sulfopolyester is preferably applied in the form of a nail coating composition comprising two aqueous emulsions. Aqueous Emulsion (A) contains a sulfopolyester and a copolymer containing vinyl acetate and a dialkyl maleate or fumarate, wherein the copolymer is polymerized in an aqueous dispersion of the sulfopolyester.

The sulfopolyester in Aqueous Emulsion (A) may be a colored sulfopolyester as described herein or an uncolored water-dispersible sulfopolyester. The colored sulfopolyester may also be blended with up to 95 weight % of an uncolored water-dispersible sulfopolyester. Suitable uncolored water-dispersible sulfopolyesters comprise the reaction residues of a dicarboxylic acid, a diol, and a difunctional sulfomonomer, as described herein, and the ester-forming and esteramide-forming derivatives thereof. Uncolored water-dispersible sulfopolyesters are commercially available from Eastman Chemical Company as Eastman AQ29D, 38D, 38S, 48 Ultra, 55D and 55S. Alternatively, the colored sulfopolyester may be added after Aqueous Emulsions (A) and (B) have been combined.

The copolymer, component (2), has repeat units from 50 to 90 weight percent vinyl acetate and 10 to 50 weight percent of a dialkyl maleate or fumarate. The dialkyl maleate or fumarate has the formula:

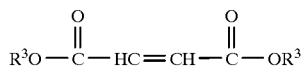

wherein each $R^3$ is independently a $C_1$–$C_{10}$ alkyl group. The vinyl acetate and dialkyl maleate or fumarate are polymerized in an aqueous dispersion containing the sulfopolyester (1), to form a copolymer (2). Preferably, the dialkyl maleate is dibutyl maleate.

It is preferred that the copolymer (2) be comprised of units derived from vinyl acetate present at levels at about 80 weight percent and units derived from a dialkyl maleate present at levels of about 20 weight percent. It is also preferred that aqueous emulsion (A) consist of from about 5 to about 20 weight percent of sulfopolyester (1) and from about 80 to about 95 weight percent of copolymer (2).

Aqueous Emulsion (B) contains acetoacetoxyethyl alkylacrylate having Formula (I):

wherein $R^4$ is a $C_1$–$C_4$ alkyl group. Preferably, the acetoacetoxyethyl alkylacrylate is acetoacetoxyethyl methacrylate. Aqueous Emulsion (B) may also contain a reaction product of acetoacetoxyethyl alkylacrylate with a vinylfunctional monomer of Formula II, III and IV below:

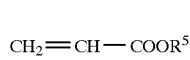

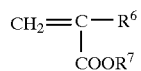

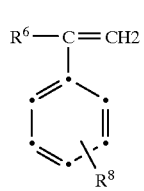

and mixtures thereof; wherein $R^5$ is selected from unsubstituted or substituted $C_1$–$C_{10}$ alkyl groups, $C_3$–$C_8$ cycloalkyl, phenyl and substituted phenyl; $R^6$ is hydrogen or methyl; $R^7$ is $C_1$–$C_{10}$ alkyl or $C_1$–$C_{10}$ alkylene-$N(R^9)R^{10}$, wherein $R^9$ and $R^{10}$ are independently selected from hydrogen, $C_1$–$C_2$ alkyl and hydroxy $C_1$–$C_4$ alkyl; and $R^8$ is hydrogen or $C_1$–$C_6$ alkyl.

The term "substituted phenyl" refers to a phenyl radical substituted with one or more groups selected from $C_1$ to $C_4$ alkyl, $C_1$ to $C_4$ alkoxy, and halogen. Examples of substituted phenyl groups are 4-methylphenyl, 3,4-dimethylphenyl, 3-methylphenyl, 2-chlorophenyl, 4-chlorophenyl, 2,5-dichlorophenyl, 4-ethoxyphenyl, 4-n-butylphenyl, 3-isopropoxyphenyl, 4-t-butyloxyphenyl, 2-ethoxy-5-methylphenyl and 2,5-diethoxyphenyl.

Mixtures of such vinylfunctional monomers may also be reacted with acetoacetoxyethyl methacrylate and used as Aqueous Emulsion (B). Aqueous Emulsion (B) is present in an amount of from 15 to 70 weight percent, preferably 15 to 25 weight percent based on the total weight of Aqueous Emulsions (A) and (B).

Examples of suitable acrylate esters, Formula II, are methyl acrylate, ethyl acrylate, butyl acrylate, benzyl acrylate, furfuryl acrylate, tetrahydrofurfuryl acrylate, methoxyethyl acrylate, ethoxyethyl acrylate, 2-ethylhexyl acrylate, cyclopentyl acrylate, cyclohexyl acrylate, 2,3-epoxy-1-propyl acrylate, 2-dimethylaminoethyl acrylate, and lauryl acrylate.

Examples of suitable methacrylate esters, Formula III, are methyl methacrylate, ethyl methacrylate, propyl methacrylate, butyl methacrylate, phenyl methacrylate, benzyl methacrylate, propyleneglycol monomethacrylate, stearyl methacrylate, tetrahydrofurfuryl methacrylate, furfuryl methacrylate, 2-diethylaminoethyl methacrylate and hydroxyethyl methacrylate.

Examples of suitable aromatic vinylfunctional monomers, formula IV, are styrene, 4-vinyltoluene, 2-vinyltoluene, a-methylstyrene, 4-isopropylstyrene, and diisopropenyl benzene.

In addition to the above three classes of vinylfunctional monomers, Formulas II, III and IV, additional optional vinylfunctional monomers may be reacted with acetoacetoxyethyl alkylacrylate, however, the total amount of any of the optional vinylfunctional monomers should not exceed 10 percent by weight of the vinylfunctional monomers of Formulas II, III and IV, and should preferably be less than 5 percent by weight. The specific nature of the optional vinylfunctional monomer is not critical so long as the amount of any optional vinylfunctional monomer does not deleteriously affect the film forming properties of the compositions.

It has been discovered that the adhesion and durability of the nail coating compositions utilizing the film forming compositions of the present invention may be improved by incorporating a fixing or crosslinking agent into the compositions of the present invention. The fixing or crosslinking agent is preferably applied directly to the nails before the application of the nail coating composition. Alternatively, the fixing or crosslinking agent may be incorporated into the nail coating composition prior to applying the nail coating composition to the nails. The fixing or crosslinking agents may be dissolved in water, acetone or a mixture of water and acetone at levels of about 1 to about 10 weight percent. Preferred are solutions containing about 1% $ZnCl_2$, 4% water and 95% acetone, percentages by weight, or a solution containing 90 to 95 weight percent acetone and 5 to 10 weight percent of a triamine.

Useful fixing or crosslinking agents include divalent metals, trivalent metals, aldehydes, amino acids, diamines and triamines. Specific examples include zinc chloride, zinc acetate, formaldehyde, alanine and cystine. Preferred amines contain a polymeric portion consisting of poly(oxyalkylene), such as JEFFAMINE 600 and 2000, available from Texaco Chemical Company. Formaldehyde has been found to be especially effective as a fixing agent in the case where a fixing agent is incorporated into a nail coating composition which contains the compositions of the present invention prior to applying the nail coating composition to the nails.

Many other ingredients may be added to the nail coating compositions of the present invention to enhance the performance properties of the nail coating. For example, preservatives, dispersing agents, wetting agents, coalescing agents, antifoams, buffers, chelating agents, ultraviolet light absorbing agents, stabilizers, fillers, thickeners such as bentonite, opacifiers such as titanium dioxide, guanine, bismuth oxychloride, and pearlescent pigments, etc., may be included herein usually up to about 5.0% by weight of the total composition. All of these additives and the use thereof are well known in the art. Any of these compounds can be used so long as they do not hinder the present invention from accomplishing its objects.

Aqueous Emulsions (A) and (B) are prepared as aqueous emulsion polymers. In the case of Aqueous Emulsion (A), the vinyl acetate and dialkyl maleate are added to an aqueous dispersion of the sulfopolyester and polymerized by free radical initiation in conventional emulsion or suspension polymerization processes. The polymerization can be initiated by a water-soluble free radical initiator known in the art such as sodium persulfate or by an oil-soluble initiator such as benzoyl peroxide. Other useful initiators include non-redox initiators, such as persulfate salts, hydrogen peroxide, and organic peroxides; redox initiators, such as sodium persulfate, sodium bisulfite, sodium metabisulfite, sodium hydrosulfite, sodium thiosulfate, and sodium formaldehyde sulfoxylate. Redox initiators require an activator, such as ferrous sulfate heptahydrate, and ferrous ammonium sulfate. The preferred initiators are persulfate salts, sodium formaldehyde sulfoxylate, and ferrous sulfate heptahydrate.

The colored sulfopolyesters which are used in the present invention typically become very viscous at concentrations above 30 percent solids. Thus, the reaction typically is begun with a sulfopolyester dispersion that is about 30 percent total solids or less. However, the water-dispersible sulfopolyester dispersions which are prepared by the process of the present invention can be prepared at final total solids levels up to about 65 percent. The increase in solids level is achieved during polymerization by controlling the amount of water, if any, which is added along with the vinyl acetate and dialkyl maleate. By decreasing the amount of water added during the polymerization, increasing total solids contents up to about 65 percent is possible.

In a preferred embodiment, the colored sulfopolyester is prepared by melt polymerization, and an aqueous dispersion containing about 5–35 weight percent, preferably from about 10 percent to 30 percent total solids, is prepared from the sulfopolyester directly. A mixture of the vinyl acetate, dialkyl maleate and the polymerization initiators are then added to the aqueous dispersion of the sulfopolyester and polymerization initiated to produce an aqueous dispersion. The aqueous dispersion so produced can be prepared with total solids contents from about 10 percent to about 65 percent.

In the case of Aqueous Emulsion (B), the acetoacetoxyethyl methacrylate alone or in combination with a vinyl-functional monomer of Formula II, III or IV, is combined with water, initiator and surfactant, and polymerized by free radical initiation in conventional emulsion or suspension polymerization processes. The polymerization can be initiated by a water-soluble free radical initiator known in the art such as sodium persulfate or by an oil-soluble initiator such as benzoyl peroxide. Other useful initiators include non-redox initiators, such as persulfate salts, hydrogen peroxide, and organic peroxides; redox initiators, such as sodium persulfate, sodium bisulfite, sodium metabisulfite, sodium hydrosulfite, sodium thiosulfate, and sodium formaldehyde sulfoxylate. Redox initiators require an activator, such as ferrous sulfate heptahydrate, and ferrous ammonium sulfate. The preferred initiators are persulfate salts, sodium formaldehyde sulfoxylate, and ferrous sulfate heptahydrate.

More than one surfactant may be used including a combination of anionic and non-anionic surfactants. cationic surfactants are rarely used. The anionic and non-anionic surfactants are preferred. Examples of suitable non-ionic surfactants are alcohol-ethylene oxide condensates, fatty acid-ethylene oxide condensates, phenol-ethylene oxide condensates, modified alkyl resins, and sorbitol-fatty acid adducts. Preferred non-ionic surfactants are phenol-ethylene oxide condensates and modified alkyl resins. Examples of suitable anionic surfactants are polyether sulfonates, dialkyl sulfosuccinates, alkyl and alkaryl sulfonates, dialkyl sulfosuccinamides, alkyl sulfates, and phosphate esters. Preferred anionic surfactants are polyether sulfonates and alkyl sulfonates.

To obtain the most effective utilization of the nail coating compositions of this invention, it is recommended that the nails be cleaned prior to applying the nail coating composition. Useful cleaning compounds include ethyl acetate, acetone, toluene, xylene and the like.

The following nonlimiting examples illustrate further the practice of the invention:

EXAMPLE 1

Preparation of a red polymeric colorant.

A mixture of 51.6 gram (0.27 mole) of dimethyl isophthalate, 24.9 gram (0.84 mole) of dimethyl sodium sulfoisophthalate, 58.3 gram (0.55 mole) of diethylene glycol, 11.4 gram (0.79 mole) of 1,4-cyclohexanedimethanol, 0.75 gram (0.009 mole) of sodium acetate, and 10 gram (0.024 mole) of 1,5-bis(3-hydroxy-2,2-dimethylpropylamion)anthraquinone was prepared. The mixture was placed in a round bottom flask and a sufficient amount of a 0.03 g/ml titanium in a titanium(IV)butoxide in n-butanol solution was added to provide a concentration of 75 ppm titanium in the mixture. The flask was immersed in a heating bath which had a temperature of 200° C. The temperature was increased to 220° and maintained for one hour and then increased to 250° and maintained for one hour. Vacuum was applied over a period of 15 min, then the vacuum was released and the heat was removed resulting in a solid polymeric colorant which was ground and analyzed.

Analysis of the polymeric colorant indicated a number average molecular weight ($M_N$) of 4662, and a Tg of 51.54° C. Nuclear magnetic resonance indicated that the polymeric colorant contained 9.1 weight % of the dye molecule.

EXAMPLE 2

Preparation of an aqueous nail coating composition.

The red polymeric colorant prepared in Example 1, 10 gram, was added to 90 gram of AQUAREZ 7, which contains acrylates\acetoacetoxyethyl methacrylate copolymer and sulfopolyester and is available from Eastman Chemical Company, under high shear mixing and heating to 55° C. The resulting red nail polish was applied to a fingernail. The nail polish provided a smooth, glossy coating to the fingernail.

EXAMPLE 3

Preparation of an aqueous nail coating composition.

The red polymeric colorant prepared in Example 1, 15 gram, was added to 85 gram of AQUAREZ 7 under high shear mixing and heating to 55° C. The resulting red nail polish was applied to a fingernail. The nail polish, which was more viscous than the nail polish prepared in Example 2, provided a smooth, glossy coating to the fingernail.

EXAMPLE 4

Preparation of a red polymeric colorant.

A mixture of 79.51 gram (0.41 mole) of dimethyl isophthalate, 26.64 gram (0.09 mole) of dimethyl sodium sulfoisophthalate, 54.0 gram (0.51 mole) of diethylene glycol, 37.44 gram (0.25 mole) of 1,4- cyclohexanedimethanol, 0.75 gram (0.009 mole) of sodium acetate, and 15 gram (0.036 mole) of 1,5-bis(3-hydroxy-2,2-dimethylpropylamion)anthraquinone, was prepared. The mixture was placed in a round bottom flask and a sufficient amount of a 0.03 g/ml titanium in a titanium(IV)butoxide in n-butanol solution was added to provide a concentration of 75 ppm titanium in the mixture. The flask was immersed in a heating bath which had a temperature of 200° C. The temperature was increased to 220° and maintained for one hour and then increased to 250° and maintained for one hour. Vacuum was applied over a period of 15 min, then the vacuum was released and the heat was removed resulting in a solid polymeric colorant which was ground and analyzed.

Analysis of the polymeric colorant indicated a number average molecular weight ($M_N$) of 6878, and a Tg of 60.05° C. Nuclear magnetic resonance indicated that the polymeric colorant contained 9.25 weight % of the dye molecule.

EXAMPLE 5

Preparation of an aqueous nail coating composition.

The red polymeric colorant prepared in Example 4, 10 gram, was added to 90 gram of AQUAREZ 7 under high shear mixing and heating to 55° C. The resulting red nail polish, which was much more viscous than the nail polishes prepared in Examples 2 or 3, was applied to a fingernail. The nail polish provided a smooth, glossy coating to the fingernail.

EXAMPLE 6

Preparation of a red polymeric colorant Dispersion.

A mixture of 63.27 gram (0.33 mole) of dimethyl isophthalate, 19.18 gram (0.065 mole) of dimethyl sodium sulfoisophthalate, 28.52 gram (0.27 mole) of diethylene glycol, 26.36 gram (0.18 mole) of 1,4-cyclohexanedimethanol, 0.75 gram (0.009 mole) of sodium acetate, and 35 gram (0.085 mole) of 1,5-bis(3-hydroxy-2,2-dimethylpropylamion)anthraquinone, was prepared. The mixture was placed in a round bottom flask and a sufficient amount of a 0.03 g/ml titanium in a titanium(IV)butoxide in n-butanol solution was added to provide a concentration of 75 ppm titanium in the mixture. The flask was immersed in a heating bath which had a temperature of 200° C. The temperature was increased to 220° and maintained for one hour and then increased to 250° and maintained for one hour. Vacuum was applied over a period of 15 min, then the vacuum was released and the heat was removed resulting in a solid polymeric colorant which was ground and analyzed.

Analysis of the polymeric colorant indicated a number average molecular weight ($M_N$) of 5987, and a Tg of 74.46° C. Nuclear magnetic resonance analysis indicated that the polymeric colorant contained 25.3 weight % of the dye molecule.

The polymeric colorant, 110 gram, was dispersed into 275 ml of boiling deionized water to give a red polymeric colorant dispersion which contained 28% of the polymeric colorant.

EXAMPLE 7

Preparation of an aqueous nail coating composition.

A mixture was prepared containing 76% of the red polymeric colorant dispersion prepared in Example 6 and 24% of deionized water. The mixture was applied to a fingernail. The mixture covered the fingernail and formed a film. The film was removed from the fingernail by rubbing with soap and water.

EXAMPLE 8

Preparation of an aqueous nail coating composition.

A mixture was prepared by mixing 95% of the red polymeric colorant dispersion prepared in Example 6, and 5% of Eastman AQ 55s which is an uncolored sulfonated polyester at a temperature of 80° C. The uncolored sulfopolyester readily mixed into the colorant dispersion. The mixture was applied to a fingernail.

This example demonstrates that commercially available colorless, water-dispersible sulfopolyesters from Eastman Chemical Company such as Eastman AQ29D, 38D, 38S, 48D, 48S, 55D and 55S are compatible with the nail coating compositions of the present invention.

The nail coating compositions of the present invention provide films which strongly adhere to the nail surface. Moreover, the films remain flexible under different temperature and relative humidity conditions so as to withstand the bending of nails without fracturing and separating from the nail. In addition, the films remain hard enough to prevent the transfer of color if rubbed against parts of the body, clothing, etc. The films are safe and do not irritate or stain the skin.

While the invention has been described with particular reference to certain embodiments thereof, it will be understood that changes and modifications may be made which are within the skill of the art. The present invention is limited only by the claims that follow.

What is claimed is:

1. A method of coloring nails comprising applying to the nail an effective amount of at least one sulfopolyester, containing substantially equimolar proportions of acid equivalents to hydroxy equivalents, comprising the reaction residues of the following reactants and their ester-forming derivatives:

(a) a dicarboxylic acid selected from the group consisting of aromatic dicarboxylic acids, saturated aliphatic dicarboxylic acids, cycloaliphatic dicarboxylic acids, and combinations thereof;

(b) a diol;

(c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino; and (d) from 1 to 40 mole %, based on a total of all acid and hydroxy equivalents being equal to about 200 mole %, of a colorant having the formula X—Col—X, wherein Col is the colorant residue, and X is a condensable carbonyloxy-reactive or carbonylamide-reactive substituent independently selected from the group consisting of hydroxy, carboxy, amnino, alkylamino, an ester radical and an amido radical, wherein said radicals have the formula:

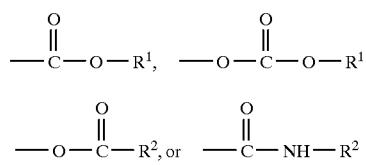

wherein $R^1$ is selected from the group consisting of $C_1$–$C_5$ alkyl, $C_3$–$C_8$ cycloalkyl and phenyl; and $R^2$ is hydrogen or $R^1$.

2. The method of claim 1 wherein X of the colorant is selected from the group consisting of hydroxy, carboxy, carbalkoxy and alkanoyloxy having up to 4 carbon atoms.

13

3. The method of claim 2 wherein X is selected from the group consisting of carbomethoxy and acetoxy.

4. The method of claim 1 wherein the colorant is selected from the group consisting of:

methines, bis-methines, anthraquinones, 3H-dibenz[f,ij] isoquinoline-2,7-diones(anthrapyridones), triphenodioxazines, 5,12-dihydroquinoxalino[2,3-b] phenazines(fluorindines), phthaloylpyrrocolines, 2H-1-benzopyran-2-ones(coumarins), 3H-naphtho[2,1-b]pyran-2-ones(benzocoumarins), 4-amino-1,8 naphthalimides, thioxanthene-9-ones, 2,5(3)-arylaminoterephthalic acids (or esters), benzo[f]pyrido[1,2-a]indole-6,11-diones, quinophthalones, 7H-benz(de)anthracene-7-ones(benzanthrones), 7H-benzo[e]perimidin-7-ones (anthrapyrimidines), 6,15-dihydro-5,9,14,18-anthrazinetetrones (indanthrones), 7H-dibenz[f,ij]isoquinoline-7-ones (anthrapyridines), 6H,18H-pyrido[1,2-a:3,4-b']diindole-6,13-diones, diindolo[3,2,1-de:3',2',1'-ij][1,5]naphthpyridin-6,13-diones, naphtho[1',2',3':4,5]quino[2,1-b]quinazoline-5,10 diones, benzo[f]pyrido[1,2-a]indole-6,11-diones, 7H-benzimidazo[2,1-a][de]isoquinolin-7-one, 5H-benzol[a]phenoxazine-5-ones, 5H-benzo[a]phenothiazine-5-ones, benzo[f]pyrido[1,2-a]indole-6,11-diones, 3,6-diaminopyromellitic acid diimides, naphthalene[1:4:5:8]tetra carboxylic bis imides, 3-aryl-2,5-dioxypyrrolines, perinones, perylenes, phthalocyanines, anthraisothiazoles, quinacridones, anthrapyrimidones, phthaloylacridones, phthaloylphenothiazines, phthaloylphenothiazine-S,S-dioxides, and combinations thereof.

5. The method of claim 4 wherein the colorant is selected from the group consisting of methines, bis-methines, anthrapyridones, anthraquinones and phthalocyanines.

6. The method of claim 1 wherein the inherent viscosity of the sulfopolyester is from about 0.10 to about 0.50 dL/g.

7. The method of claim 6 wherein the sulfopolyester has a number average molecular weight of from about 3,000 to about 15,000.

8. An aqueous nail coating composition comprising:
(A) a first water-dispersible, sulfopolyester containing substantially equimolar proportions of acid equivalents to hydroxy equivalents, comprising the reaction residues of the following reactants and their ester-forming derivatives:
   (a) a dicarboxylic acid selected from the group consisting of aromatic dicarboxylic acids, saturated aliphatic dicarboxylic acids, cycloaliphatic dicarboxylic acids, and combinations thereof;
   (b) a diol;
   (c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino; and
   (d) from 1 to 40 mole %, based on a total of all acid and hydroxy equivalents being equal to about 200 mole %, of a colorant having the formula X—Col—X, wherein Col is the colorant residue, and X is a condensable carbonyloxy-reactive or carbonylamide-reactive substituent independently selected from the group consisting of hydroxy, carboxy, amino, alkylamino, an ester radical and an amido radical, wherein said radicals have the formula:

14

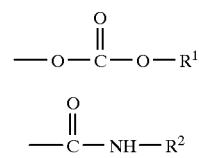

wherein $R^1$ is selected from the group consisting of $C_1$–$C_5$ alkyl, $C_3$–$C_8$ cycloalkyl and phenyl; and $R^2$ is hydrogen or $R^1$; and (B) an aqueous emulsion which comprises:
   (1) a second water dispersible sulfopolyester;
   (2) a copolymer having repeat units from 50 to 90 weight percent vinyl acetate and 10 to 50 weight percent of a dialkyl maleate or fumarate having the formula:

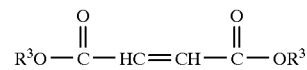

wherein $R^3$ is independently a $C_1$–$C_{10}$ alkyl group; and
   (3) an acetoacetoxyethyl alkylacrylate having the formula:

wherein $R^4$ is a $C_1$–$C_4$ alkyl group,
provided the aqueous nail coating composition has a total solids content of from about 30 to about 65 weight percent.

9. An aqueous nail coating composition comprising:
(A) 30 to 85 weight percent of an aqueous emulsion comprising
   (1) a sulfopolyester containing substantially equimolar proportions of acid equivalents to hydroxy equivalents, comprising the reaction residues of the following reactants and their ester-forming derivatives:
      (a) a dicarboxylic acid selected from the group consisting of aromatic dicarboxylic acids, saturated aliphatic dicarboxylic acids, cycloaliphatic dicarboxylic acids, and combinations thereof;
      (b) a diol;
      (c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino; and
      (d) from 1 to 40 mole %, based on a total of all acid and hydroxy equivalents being equal to about 200 mole %, of a colorant having the formula X—Col—X,
         wherein Col is the colorant residue, and X is a condensable carbonyloxy-reactive or carbonylamide-reactive substituent independently selected from the group consisting of hydroxy, carboxy, amino, alkylamino, an ester radical and an amido radical, wherein said radicals have the formula:

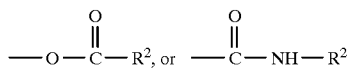

wherein $R^1$ is selected from the group consisting of $C_1$–$C_5$ alkyl, $C_3$–$C_8$ cycloalkyl and phenyl; and $R^2$ is hydrogen or $R^1$; and (2) a copolymer having repeat units from 50 to 90 weight percent vinyl acetate and 10 to 50 weight percent of a dialkyl maleate or fumarate having the formula:

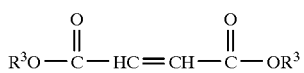

which is polymerized in an aqueous dispersion of the sulfopolyester, wherein $R^3$ is independently a $C_1$–$C_{10}$ alkyl group; and (B) 15 to 70 weight percent of an aqueous emulsion containing acetoacetoxyethyl alkylacrylate having the formula:

or a reaction product of acetoacetoxyethyl alkylacrylate with a vinylfunctional monomer selected from the group consisting of:

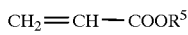

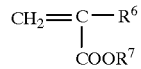

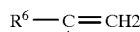

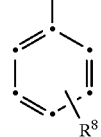

and mixtures thereof;
wherein $R^4$ is a $C_1$–$C_4$ alkyl group; $R^5$ is selected from the group consisting of $C_1$–$C_{10}$ alkyl group, $C_3$–$C_8$ cycloalkyl and phenyl; $R^6$ is hydrogen or methyl; $R^7$ is $C_1$–$C_{10}$ alkyl or $C_1$–$C_{10}$ alkylene-N($R^9$)$R^{10}$, wherein $R^9$ and $R^{10}$ are independently selected from the group consisting of hydrogen, $C_1$–$C_2$ alkyl and hydroxy $C_1$–$C_4$ alkyl; and $R^8$ is hydrogen or $C_1$–$C_6$ alkyl, provided that the total solids in the nail coating composition is from 30 to 65 weight percent.

10. The aqueous nail coating composition of claim 8 which additionally contains a fixing agent.

11. The aqueous nail coating composition of claim 10 wherein the fixing agent is selected from the group consisting of divalent metals, trivalent metals, aldehydes, amino acids, diamines and triamines.

12. The aqueous nail coating composition of claim 9 wherein the dicarboxylic acid is selected from the group consisting of terephthalic acid, phthalic acid, isophthalic acid, naphthalene-2,6-dicarboxylic acid, cyclohexanedicarboxylic acid, cyclohexanediacetic acid, and mixtures thereof.

13. The aqueous nail coating composition of claim 12 wherein the dicarboxylic acid is isophthalic acid.

14. The aqueous nail coating composition of claim 9 wherein the diol is selected from the group consisting of ethylene glycol, diethylene glycol, triethylene glycol, 1,4-cyclohexanedimethanol, and mixtures thereof.

15. The aqueous nail coating composition of claim 14 wherein the diol is diethylene glycol and 1,4-cyclohexanedimethanol.

16. The aqueous nail coating composition of claim 15 wherein the difunctional sulfomonomer is selected from the group consisting of sulfophthalic acid, sulfoterephthalic acid, sulfoisophthalic acid, 4-sulfonaphthalene-2,7-dicarboxylic acid, and their esters.

17. The aqueous nail coating composition of claim 16 wherein the difunctional sulfomonomer is 5-sodiosulfoisophthalic acid.

18. The aqueous nail coating composition of claim 9 wherein the acetoacetoxyethyl alkylacrylate is acetoacetoxyethyl methacrylate.

19. The aqueous nail coating composition of claim 9 wherein the vinylfunctional monomer is selected from the group consisting of acrylate esters, methacrylate esters, aromatic vinylfunctional monomers and mixtures thereof.

20. The aqueous nail coating composition of claim 19 wherein the vinylfunctional monomer is an acrylate ester selected from the group consisting of methyl acrylate, ethyl acrylate, butyl acrylate, benzyl acrylate, furfuryl acrylate, tetrahydrofurfuryl acrylate, methoxyethyl acrylate, ethoxyethyl acrylate, 2-ethylhexyl acrylate, cyclopentyl acrylate, cyclohexyl acrylate, 2,3-epoxy-1-propyl acrylate, 2-dimethylaminoethyl acrylate, lauryl acrylate, and mixtures thereof.

21. The aqueous nail coating composition of claim 19 wherein the vinylfunctional monomer is a methacrylate ester selected from the group consisting of methyl methacrylate, ethyl methacrylate, propyl methacrylate, butyl methacrylate, phenyl methacrylate, benzyl methacrylate, propyleneglycol monomethacrylate, stearyl methacrylate, tetrahydrofurfuryl methacrylate, furfuryl methacrylate, 2-diethylaminoethyl methacrylate, hydroxyethyl methacrylate, and mixtures thereof.

22. The aqueous nail coating composition of claim 21 wherein the vinylfunctional monomer is selected from the group consisting of butyl acrylate, methyl methacrylate, ethyl acrylate and mixtures thereof.

23. The aqueous nail coating composition of claim 19 wherein the vinylfunctional monomer is an aromatic vinylfunctional monomer selected from the group consisting of styrene, 4-vinyltoluene, 2-vinyltoluene, a-methylstyrene, 4-isopropylstyrene, diisopropenyl benzene, and mixtures thereof.

24. A method of preparing an aqueous nail coating composition comprising:
(I) preparing a sulfopolyester containing substantially equimolar proportions of acid equivalents to hydroxy equivalents, comprising the reaction residues of the following reactants and their ester-forming derivatives:
(a) a dicarboxylic acid selected from the group consisting of aromatic dicarboxylic acids, saturated aliphatic dicarboxylic acids, cycloaliphatic dicarboxylic acids, and combinations thereof;

(b) a diol;

(c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino; and (d) from 1 to 40 mole %, based on a total of all acid and hydroxy equivalents being equal to about 200 mole %, of a colorant having the formula X—Col—X, wherein Col is the colorant residue, and X is a condensable carbonyloxy-reactive or carbonylamide-reactive substituent independently selected from the group consisting of hydroxy, carboxy, amino, alkylamino, an ester radical and an amido radical, wherein said radicals have the formula:

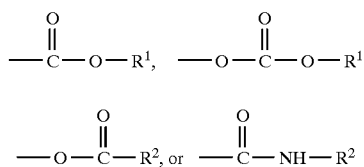

wherein $R^1$ is selected from the group consisting of $C_1$–$C_5$ alkyl, $C_3$–$C_8$ cycloalkyl and phenyl; and $R^2$ is hydrogen or $R^1$; and (II) forming an Aqueous Emulsion (A) which contains the sulfopolyester prepared in Step (I), and polymerizing a copolymer having repeat units from 50 to 90 weight percent vinyl acetate and 10 to 50 weight percent of a dialkyl maleate or fumarate having the formula:

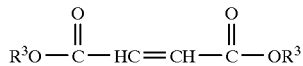

in an aqueous dispersion of the sulfopolyester, wherein $R^3$ is independently a $C_1$–$C_{10}$ alkyl group; and independently (III) preparing an Aqueous Emulsion (B) containing acetoacetoxyethyl alkylacrylate having the formula:

or a reaction product of acetoacetoxyethyl alkylacrylate with a vinylfunctional monomer selected from the group consisting of:

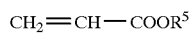

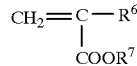

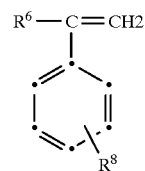

and mixtures thereof;

wherein R is a $C_1$–$C_4$ alkyl group; $R^5$ is selected from the group consisting of $C_1$–$C_{10}$ alkyl group, $C_3$–$C_8$ cycloalkyl and phenyl; $R^6$ is hydrogen or methyl; $R^7$ is $C_1$–$C_{10}$ alkyl or $C_1$–$C_{10}$ alkylene-N($R^9$)$R^{10}$, wherein $R^9$ and $R^{10}$ are independently selected from the group consisting of hydrogen, $C_1$–$C_2$ alkyl and hydroxy $C_1$–$C_4$ alkyl; and $R^8$ is hydrogen or $C_1$–$C_6$ alkyl; and (IV) mixing Aqueous Emulsions (A) and (B) to thereby obtain an aqueous nail coating composition with a total solids content of from about 30 to about 65 weight percent.

25. The method of claim 24 wherein prior to mixing Aqueous Emulsions (A) and (B) in Step (IV), a fixing agent is added to Aqueous Emulsion (B).

26. A method of preparing an aqueous nail coating composition comprising:

(I) preparing a first sulfopolyester containing substantially equimolar proportions of acid equivalents to hydroxy equivalents, comprising the reaction residues of the following reactants and their ester-forming derivatives:

(a) a dicarboxylic acid selected from the group consisting of aromatic dicarboxylic acids, saturated aliphatic dicarboxylic acids, cycloaliphatic dicarboxylic acids, and combinations thereof;

(b) a diol; and (c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino;

(II) forming an Aqueous Emulsion (A) which contains the first sulfopolyester prepared in Step (I), and polymerizing a copolymer having repeat units from 50 to 90 weight percent vinyl acetate and 10 to 50 weight percent of a dialkyl maleate or fumarate having the formula:

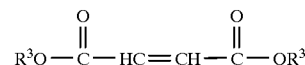

in an aqueous dispersion of the first sulfopolyester, wherein $R^3$ is independently a $C_1$–$C_{10}$ alkyl group; and independently (III) preparing an Aqueous Emulsion (B) containing acetoacetoxyethyl alkylacrylate having the formula:

or a reaction product of acetoacetoxyethyl alkylacrylate with a vinylfunctional monomer selected from the group consisting of:

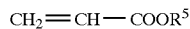

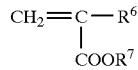

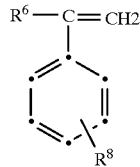

and mixtures thereof;

wherein $R^4$ is a $C_1$–$C_4$ alkyl group; $R^5$ is selected from the group consisting of $C_1$–$C_{10}$ alkyl group, $C_3$–$C_8$ cycloalkyl and phenyl; $R^6$ is hydrogen or methyl; $R^7$ is $C_1$–$C_{10}$ alkyl or $C_1$–$C_{10}$ alkylene-$N(R^9)R^{10}$ wherein $R^9$ and $R^{10}$ are independently selected from the group consisting of hydrogen, $C_1$–$C_2$ alkyl and hydroxy $C_1$–$C_4$ alkyl; and $R^8$ is hydrogen or $C_1$–$C_6$ alkyl;

(IV) mixing Aqueous Emulsions (A) and (B) to form an emulsion mixture; and (V) adding a second sulfopolyester containing substantially equimolar proportions of acid equivalents to hydroxy equivalents to the emulsion mixture formed in Step (IV) to thereby obtain an aqueous nail coating composition with a total solids content of from about 30 to about 65 weight percent, said second sulfopolyester comprising the reaction residues of the following reactants and their ester-forming derivatives:

(a) a dicarboxylic acid selected from the group consisting of aromatic dicarboxylic acids, saturated aliphatic dicarboxylic acids, cycloaliphatic dicarboxylic acids, and combinations thereof;

(b) a diol;

(c) from about 4 to about 25 mole %, based on a total of all acid and hydroxy equivalents being equal to about 200 mole %, of a difunctional sulfomonomer containing at least one sulfonate group attached to an aromatic nucleus or cycloaliphatic nucleus wherein the functional groups are selected from the group consisting of hydroxy, carboxy and amino; and (d) from 1 to 40 mole %, based on a total of all acid and hydroxy equivalents being equal to about 200 mole %, of a colorant having the formula X—Col—X, wherein Col is the colorant residue, and X is a condensable carbonyloxy-reactive or carbonylamide-reactive substituent independently selected from the group consisting of hydroxy, carboxy, amino, alkylamino, an ester radical and an amido radical, wherein said radicals have the formula:

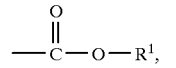 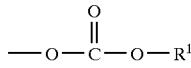

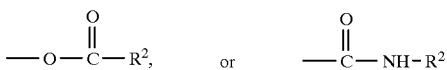

wherein $R^1$ is selected from the group consisting of $C_1$–$C_5$ alkyl, $C_3$–$C_8$ cycloalkyl and phenyl; and $R^2$ is hydrogen or $R^1$.

27. A method of preparing an aqueous nail coating composition comprising mixing:

(A) a first water-dispersible, sulfopolyester containing substantially equimolar proportions of acid equivalents to hydroxy equivalents, comprising the reaction residues of the following reactants and their ester-forming derivatives:

(a) a dicarboxylic acid selected from the group consisting of aromatic dicarboxylic acids, saturated aliphatic dicarboxylic acids, cycloaliphatic dicarboxylic acids, and combinations thereof;

(b) a diol;

(c) from about 4 to about 25 mole %, based on a total of all acid and hydroxy equivalents being egual to about 200 mole %, of a difunctional sulfomonomer containing at least one sulfonate group attached to an aromatic nucleus or cycloaliphatic nucleus wherein the functional groups are selected from the group consisting of hydroxy, carboxy amino; and (d) from 1 to 40 mole %, based on a total of all acid and hydroxy equivalents being equal to about 200 mole % of a colorant having the formula X—Col—X, wheren Col is the colarant relsidue, and X is a condensable carbonyloxy-reactive or carbonylamide-reactive substituent independently selected from the group consisting of hydroxy, carboxy, amino, alkylamino, an ester radical and an amido radical, wherein said radicals have the formula:

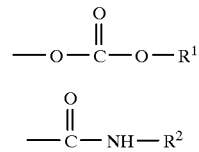

wherein $R^1$ is selected from the group consisting of $C_1$–$C_5$ alkyl, $C_3$–$C_8$ cycloalkyl and phenyl; and $R^2$ is hvdrogen or $R^1$; and (B) an aqueous emulsion which comprises:

(1) a second water-dispersible sulfopolyester;

(2) a copolymer having repeat units from 50 to 90 weight percent vinyl acetate and 10 to 50 weight percent of a dialkyl maleate or fumarate having the formula:

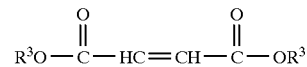

wherein $R^3$ is independently a $C_1$–$C_{10}$ alkyl group; and (3) an acetoacetoxyethyl alkylacrylate having the formula:

wherein $R^4$ is a $C_1$–$C_4$ alkyl group, to obtain an aqueous nail coating composition with a total solids content of from about 30 to about 65 weight percent.

28. The method of claim 1, wherein the colorant is selected from anthraquinones.

29. The method of claim 4, wherein the colorant is selected from anthraquinones.

30. The aqueous nail coating composition according to claim 9, wherein the colorant is selected from anthraquinones.

31. The method of claim 24, wherein the colorant is selected from anthraquinones.

32. The method of claim 28, wherein the colorant is 1,5-bis(3-hydroxy-2,2-dimethylpropylamine) anthraquinone.

33. The method of claim 29, wherein the colorant is 1,5-bis(3-hydroxy-2,2-dimethylpropylamine) anthraquinone.

34. The aqueous nail composition according to claim 30, wherein the colorant is 1,5-bis(3-hydroxy-2,2-dimethylpropylamine)anthraquinone.

35. The method of claim 31, wherein the colorant is 1,5-bis(3-hydroxy-2,2-dimethylpropylamine) anthraquinone.

36. An aqueous nail coating composition comprising a first water-dispersible sulfopolyester and a colorant reacted into or onto the first sulfopolyester backbone, prepared by reacting dimethyl isophthalate, dimnethyl sodium sulfoisophthalate, diethylene glycol, 1,4-cyclohexanedimethanol, sodium acetate, and 1,5-bis(3-hydroxy-2,2-dimethylpropylamine) anthroquinone and then mixing with a composition including a second sulfopolyester and a copolymer consisting essentially of acrylates and acetoacetoxyethyl methacrylate.

37. The method according to claim 32, including applying to human nails a composition comprising said sulfopolyester and further comprising a cross-linking agent.

38. The method according to claim 32, including applying to human nails a cross-linking agent prior to applying a composition comprising said sulfopolyester.

39. The method according to claim 32, further comprising the step of washing said nail coloring from human nails with a solution consisting essentially of soap and water.

* * * * *

UNITED STATES PATENT AND TRADEMARK OFFICE
CERTIFICATE OF CORRECTION

PATENT NO. : 5,925,336
DATED : July 20, 1999
INVENTOR(S) : Dennis Michael Garber and James John Krutak, Sr.

It is certified that error appears in the above-identified patent and that said Letters Patent is hereby corrected as shown below:

Column 12, line 50 (Claim 1, line 25), "amnino," should be --- amino ---.

Column 18, line 11 (Claim 24, line 87), "wherein R" should be
--- wherein $R^4$ ---.

Column 22, line 2 (Claim 36, line 4), "dimnethyl" should be
--- dimethyl ---.

Signed and Sealed this

Twenty-third Day of November, 1999

*Attest:*

Q. TODD DICKINSON

*Attesting Officer*       *Acting Commissioner of Patents and Trademarks*